United States Patent [19]

Cohen et al.

[11] Patent Number: 5,589,575
[45] Date of Patent: Dec. 31, 1996

[54] PURIFICATION OF HAPTEN-CARRIER GENERATED ANTIBODIES

[75] Inventors: Huguette Cohen; Ross E. Williams, both of Ottawa, Canada

[73] Assignee: Her Majesty the Queen in right of Canada, as represented by the Minister of Agriculture, Ottawa, Canada

[21] Appl. No.: 300,517

[22] Filed: Sep. 6, 1994

Related U.S. Application Data

[63] Continuation-in-part of Ser. No. 917,394, Jul. 23, 1992, abandoned, and Ser. No. 56,797, May 4, 1993, abandoned.

[51] Int. Cl.$^6$ .............................. C07K 1/22; C07K 16/00
[52] U.S. Cl. ............................ 530/413; 530/412
[58] Field of Search ...................... 530/412, 413

[56] References Cited

U.S. PATENT DOCUMENTS

| | | | |
|---|---|---|---|
| 4,230,685 | 10/1980 | Senyei et al. | 436/526 |
| 4,546,161 | 10/1985 | Harvey et al. | 527/312 |
| 4,777,145 | 10/1988 | Luotola et al. | 436/526 |
| 4,780,423 | 10/1988 | Bluestein et al. | 436/527 |
| 4,865,997 | 9/1989 | Stoker | 436/541 |
| 4,940,734 | 7/1990 | Ley et al. | 530/413 |

FOREIGN PATENT DOCUMENTS

| | | |
|---|---|---|
| 2003942 | 3/1991 | Canada . |
| 2101148 | 1/1994 | Canada . |

OTHER PUBLICATIONS

W. H. Scouten "Affinity Chromatography", 1981, John Wiley & Sons, New York, N.Y., US, p. 272, Line 1–p. 276, Line 7.

Annales Pharmaceutiques Francaises, vol. 35, No. 7–8, 1977, Paris, Fr., pp. 257–264; Pham Huy Chuong et al. "Etude des Anticorps Anti–Aspirine . . . ".

Journal Of Immunology, vol. 116, No. 5, May 1976, Baltimore, U.S. pp. 1337–1341; D. S. Terman et al. "Specific Removal Of Bovine . . . ".

*Primary Examiner*—Toni R. Scheiner
*Attorney, Agent, or Firm*—Larson And Taylor

[57] ABSTRACT

In the commonly used method to obtain antibodies to small molecules, a combination of a highly antigenic carrier, such as bovine serum albumin, and the small molecule is injected into a host animal. The recovered crude serum or plasma then contains, in addition to the desired small molecule antibodies, much larger amounts of carrier-induced antibodies. These unwanted antibodies are efficiently removed from the crude serum or plasma, by contacting the crude serum or plasma with the carrier material in an immobilized high surface area form. Rapid and efficient anticarrier antibody removal results, with minimal loss of both desired antibody, and desired antibody activity.

7 Claims, 5 Drawing Sheets

PURIFICATION OF HAPTEN-CARRIER GENERATED ANTIBODIES

This Application is a continuation-in-part of application Ser. No. 07/917,394, filed Jul. 23, 1992, now abandoned, and of application Ser. No. 08/056,797, filed May 4, 1993 now abandoned.

This invention is concerned with a method whereby an antibody mixture, including a desired antibody, obtained as a crude serum, or plasma, from a host animal may be purified to recover in high yield, and at high activity, the desired antibody. Antibodies with binding affinity for small molecular weight compounds are used for several purposes, such as immunological techniques. These small molecules generally are not themselves antigenic. Antibodies for these small molecules are generally prepared by the following method:

(i) a quantity of the compound is bound to a carrier;
(ii) the immobilized complex thereby obtained is injected into a suitable host animal, such as a pig or rabbit;
(iii) after a suitable time period, crude serum or plasma is collected from the host animal; and
(iv) the desired antibody is separated from the collected fluid.

To maximize antibody production, a highly antigenic carrier is used. This is generally a relatively high molecular weight protein, having a molecular weight above 10,000. Commonly used carriers include bovine serum albumin, or BSA, ovalbumin, keyhole limpet haemocyanin and multiple antigen peptide constructs containing T and B cell epitopes. This method produces three different antibodies:

(a) antibodies against the carrier itself;
(b) antibodies against the compound—carrier link; and
(c) antibodies against the small molecular weight compound itself.

Since a highly antigenic carrier is used, the anticarrier antibodies predominate. To obtain the desired antibodies a separation or purification procedure has to be used. This procedure must both maximize unwanted antibody removal, and minimize loss of wanted antibodies. It should also not adversely affect the activity of the desired antibody. It is also very desirable that any separation or purification procedure be reasonably fast, reliable, reproducible, and preferably also capable of use on a significant scale so that reasonable quantities of the desired antibodies can be obtained.

At present, a procedure to overcome these shortcomings appears to be needed. Usually, when measurements of antibody activity are based on protein concentration, it is found that when an antibody mixture, such as that described above, is processed to recover the desired antibody, it is often recovered in low yield and with low activity or titre. This invention describes a method and materials whereby a desired antibody can be recovered from a mixture of antibodies at high yield and with high activity.

Several techniques have been proposed for recovering antibodies. The most common procedure used is affinity chromatography. In this procedure the desired antibodies are bound to the matrix of a column containing the small molecular weight compound of interest. The unwanted antibodies do not bind to the column matrix and are washed off. The desired antibodies can be removed from the column matrix by eluting the column with a mixture containing the small molecular weight compound of interest, and subsequent dialysis to remove the compound bound to the eluted antibody. In this case, the antibodies with high binding constants are lost since they strongly bind the small molecular weight compound and reluctantly lose the small molecular weight compound during the dialysis step. Alternatively, the antibodies can be recovered by changing the pH, the use of high salt concentrations, and the use of organic solvents. These processes lead to antibody losses, and to some loss of antibody activity as the very strongly bound antibodies are very difficult to recover. In all cases antibody recovery is controlled by the chromatography conditions. The process is slow, not readily adaptable to more than small scale use, and not very efficient in terms of either antibody recovery or the activity of recovered antibodies.

In some analytical and small scale methodologies, it has been proposed to remove "unwanted" antibodies, for example cross-reactive antibodies, by a chromatography procedure in which "unwanted" antibodies are bound to a powder support with a suitably reactive surface. However, this method has several significant disadvantages. First, each powder generally will only absorb one cross-reactive antibody. Consequently, a separate treatment step is needed for each unwanted antibody, and for each of which a suitably active powder has to be obtained. Second, the elution step needed to recover the wanted antibodies from the powder is both slow and inefficient. There is "wanted" antibody loss each time the process is repeated, because both of non-specific absorption by the powder, and due ti liquid hold-up in the powder. There will also often be some loss in activity of the "wanted" antibody with each repetition. Third, in each of the required elution steps the solution containing the "wanted" antibody is diluted; introduction of a concentration step again leads to losses both of "wanted" antibody, and "wanted" antibody activity. Fourth, the required "active" powders are often very expensive to prepare or to purchase. Fifth, the "active" powders often have poor handling characteristics, poor liquid flow-through, and very often a large fluid-hold-up. These features of "wanted" antibody loss, excessive fluid dilution, and a requirement to use of materials which are quite expensive, limit these procedures to small scale use.

A related procedure is used in heterogeneous binding assays. A labelled binding reagent is separated from an unlabelled reagent by contact with a specific binding reagent attached to a solid surface. The proposed surfaces include coated powders, and coated tubes and analysis wells: see U.S. Pat. Nos. 4,230,685; 4,777,145; and 4,780,423. Most of these analysis methods are not useable other than on an analytical scale. Many also involve complex, costly, and time consuming procedures, which in some cases are of doubtful reliability.

Procedures for removing a specific antibody are described in U.S. Pat. No. 4,865,997 and Canada 2,003,942. In both of these a supported form of a biologically active binder is used. U.S. Pat. No. 4,865,997 requires the use of two different supported materials as binders, and these are intended to be re-useable. Canada 2,003,942 uses a porous flat sheet material coated with a specific polymeric polyurethane, to which the bioaffinity agent(s) is attached. These both require complex preparation routes, and again are not well adapted to large scale use.

An ideal material for removing unwanted antibodies from crude serum or plasma on a large scale should be preparable from low cost materials, should have maximum unwanted antibody adsorptive capability, should be easy to prepare under straight forward standardized conditions, and should have a good shelf life. In use, it should handle easily, and be useful in both batch and through flow processes. This invention seeks to provide a material having many of these properties.

In persuading a host animal to generate desired antibodies, for example for small molecules, in order to get a good response, a highly antigenic carrier, such as BSA or one of the other carriers mentioned above, is used. This results in a crude serum or plasma containing a high titer, relatively speaking, of anticarrier antibodies, and a low titer of desired antibodies. It has now been found that these anticarrier antibodies can be removed without any attendant loss of desired antibody, or desired antibody activity, simply by re-exposing the crude serum or plasma to the carrier in a suitable high surface area immobilized form. Typical examples are as a cross-linked coating on a tube or analysis well, or in the form of cross-linked beads. The immobilized carrier then appears to remove the anticarrier antibodies selectively and efficiently, seemingly without any effect upon the desired antibody, which can then be recovered at high titer and high activity.

Thus, in a first broad embodiment, this invention seeks to provide a method for removing anticarrier antibodies from a mixture of antibodies contained in a liquid medium, which mixture was generated in a host animal in the presence of the carrier, which process comprises:

(i) contacting the liquid medium containing the antibodies mixture with a high surface area solid form of the carrier;

(ii) incubating the solid form of the carrier in contact with the antibodies mixture at a temperature, and for a time period, sufficient for adsorption of the anticarrier antibodies by the solid form of the carrier to be substantially complete; and (iii) thereafter separating the solid form of the carrier together with the adsorbed anticarrier antibodies from the liquid medium.

Thus, in the process of this invention, what is essentially the same carrier material is used twice.

It is used first, in the conventional way, as a carrier in persuading the host animal to generate the desired antibodies which are recovered in the crude serum or plasma.

It is then used again, in an immobilized form, to remove selectively the anticarrier antibodies in the recovered crude serum or plasma.

In this latter case, the high surface area solid form of the carrier is the carrier in a cross-linked form coated onto a surface.

Alternatively, the high surface area solid form of the carrier comprises the carrier in the form of beads, consisting either of the cross-linked carrier alone, or of the cross-linked carrier coated onto an inactive core.

The term "high surface area" in this context is a relative one. For a small volume of liquid, it can comprise a coated tube, a coated well, or even a coated glass rod.

Although U.S. Pat. No. 4,940,734 teaches that microporous material can be made from organic-based materials, it does not teach that microporous beaded material can be made from carrier materials. Additionally, the method of crosslinking the materials which is taught in the '734 patent would normally lead to denatured carrier protein preparations with little or no biological or immunological activity. Therefore, the preparation of microporous material by this route could lead to proteins and antibodies with poor performance characteristics. Thus, it is not obvious that a microporous material prepared from the carrier of the hapten would offer any advantage in the isolation of the desired antibodies. While it is said that the materials described in the '734 patent can be used as chromatographic material, no demonstration of this type of use is given. Therefore, the actual performance of these organically-derived materials in chromatographic analyses is not known.

It was also indicated that the microporous material formed by using information contained in the U.S. Pat. No. 4,490,734 patent could be used to separate proteins. The separation referred to is based on the physical properties of the protein, i.e., their differing electrostatic and/or hydrophobic characters. The separation described in the present specification is based on function, not on physical properties or chromatographic behaviour, as is the case in the '734 patent. This makes the present specification substantially different and unrelated to that which as is described in the '734 patent.

In the present specification purified antibodies specific to the small molecular weight compound or hapten are left behind in solution usually substantially undiluted after binding the unwanted antibodies to the immobilized form of the carrier.

In general, the conventional systems have been designed to leave the unwanted antibodies behind in the solution. Normally, the desired antibodies are then eluted from the matrix by use of harsh conditions (usually organic solvents, low pH or chaotropic salts). These harsh conditions are those which usually cause the breakdown of the antibody's structure and, thereby, its performance. This treatment also can result in the large loss of antibodies by precipitation of the denatured antibody.

The present specification does exactly the opposite. It removes the unwanted antibodies from the solution and leaves behind the wanted antibodies substantially unchanged in concentration or activity. In this regard, the present specification is unconventional.

In order to effectively carry out the process, a microporous material such as described below, comprised solely or in part of the carrier is desired. The use of a powdered form of the carrier for the purification of antibody preparations usually leads to large losses of material through hold-back of solutions within the powder. In addition, the powders are difficult to process in columns and in batch systems. The microporous material formed from the carrier offers numerous advantages over a large surface area powder since there is lower hold-up and they can be used in batch and column systems for the rapid, large scale preparation of the desired antibodies.

The most desirable microporous material is that prepared from the carrier material itself. This maximizes the amount of active material available for contacting the antibody solutions.

It has been found that a suitable, low cost, highly active microporous material can be generated from bovine serum albumin (BSA). This carrier is commonly used as a carrier in the preparation of antibodies against small molecular weight compounds. Alternate carriers, such as ovalbumin, keyhole limpet haemocyanin, or polypeptide multiple antigen peptide constructs could also be similarly prepared. The microporous bovine serum albumin can also be used as a matrix for surface coating with the other types of carriers. It has also been found that a suitable beaded form of the bovine serum albumin can be generated by treatment of a commercial activated matrix with BSA. In this latter case, although the material generated performed reasonably well, it was costly to produce.

The microporous form of the carrier meets most, if not all, of the desiderata set forth above for a useful separation reagent. This is particularly the case for one of the frequently used carriers, that is BSA.

In theory, when the carrier is a proteinaceous material, at least two different routes can be used to transform it into a suitably active high surface area form. It is well known that proteins are polymerisable with diacids, generally to provide microporous beaded materials. This method is particularly suitable for BSA. It is also known that proteins can be polymerized or made insoluble with vinylogous compounds by using chemical initiators or gamma radiation are often used to initiate the reaction.

Other proteins used as carriers include ovalbumin, and key hole limpet haemocyanin (KLH). These proteins can also be formed directly into beads in much the same way as BSA. Where a more expensive protein is used as the carrier initially, then BSA beads, onto which the more expensive carrier protein is coated or otherwise suitably attached, can be used to provide a less expensive but easily handled support.

In these polymerization procedures, the polymerized protein is readily obtained as a free flowing beaded material, in which the beads generally have a diameter in the range of from 50 microns to 150 microns (that is, 200 to 400 mesh). These bead materials, especially for BSA, are storable and stable in a dry condition. The material also can be rehydrated easily to a fully active bioaffinity agent.

The use of such material in the preparation of antibody preparations containing antibodies against small molecular weight compounds has resulted in substantial improvements in titer since the unwanted anticarrier antibodies have been removed from the preparations.

This simple method as described avoids the problems and losses associated with chromatography based methods, and allows the unwanted antibodies to be removed from the crude serum both effectively and relatively quickly: an incubation time of under 30 minutes, often 15 minutes or less, has been shown to be effective. Further, BSA is relatively inexpensive, and polymerization of it into beads or coatings is a straight forward, easily reproducible, procedure. Hence, this invention is particularly useful in the provision of anti-hapten antibody preparations for use in ELISA assays for low molecular weight compounds, such as herbicides and pesticides.

As an example of the use of microporous carrier materials for the preparation of highly active-small molecule antibodies the generation of high titer preparations of antibodies against the herbicide, 2-[4-(5-trifluoromethyl-2-pyridyloxy)phenoxy]propionic acid, also known as fluazifob or Fusilade, is described. The antibody preparations have been used directly in ELISA assays to provide a sensitive assay procedure at the micromolar level.

BRIEF DESCRIPTION OF THE DRAWINGS

In the following Examples reference is made to the Figures, in which:

In each of the graphs shown in FIGS. 2 through 5, the vertical ordinate is the absorbance reading, taken in all cases at 490 nm. The horizontal ordinate is concentration; in FIG. 3 the scale is molar; in FIGS. 2, 4 and 5 the scale is log (protein concentration in µgm/ml).

EXAMPLE 1

Antibody Preparation, Purification and Testing

Bovine serum albumin was used in a conventional manner to generate the desired anti-fluazifob antibodies. The conjugate fluazifob-BSA was prepared as follows using the route shown schematically in FIG. 1.

Fluazifob was first reacted with N-hydroxysuccinimide and with dicyclohexyl diimide (DDC) to obtain the N-hydroxysuccinimide ester, the reaction being carried out in dichloromethane containing 5% w/v pyridine. After filtration and solvent evaporation, the ester is coupled by reaction with BSA (1~5 mg/ml) in a 5% w/v sodium bicarbonate solution.

This preparation provides fluazifob directly bonded to BSA. This preparation was used to raise anti-fluazifob antibodies, using rabbits as the host animals.

Figure 2:
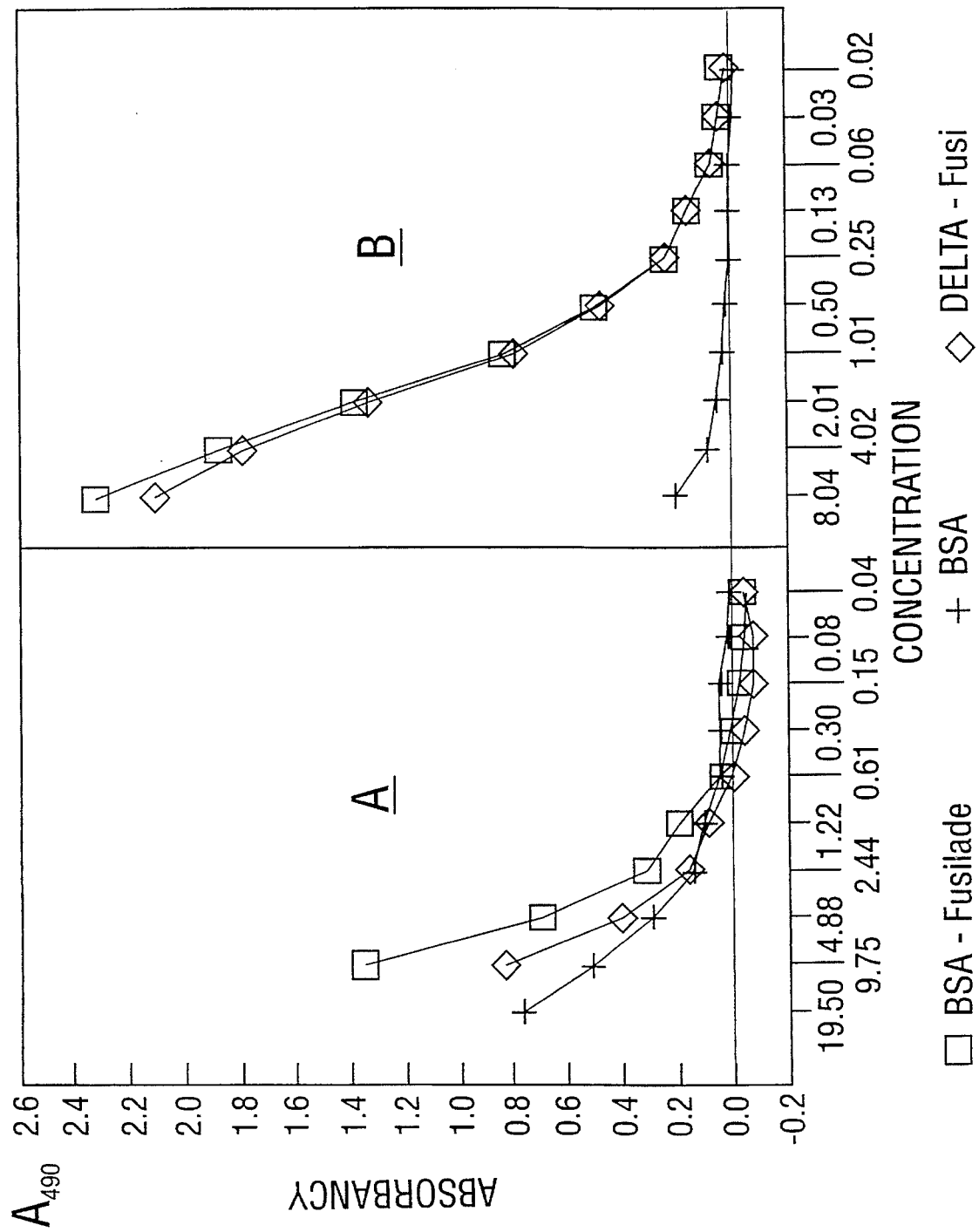
FIG. 2 represents schematically anti-fluazifob titers for the crude antibody preparation.

The anti-fluazifob titers of the crude antibody preparations were measured, and the results are shown in FIG. 2. Serum from the rabbits was treated by ammonium sulphate precipitation, followed by batch treatment with DEAE cellulose to remove extraneous proteins in order to give an IgG antibody preparation. The resulting antibodies preparation was tested for titer before and after treatment with BSA beads by the following method.

Microtiter plate wells were coated with either BSA, or a fluazifob-BSA conjugate, and aliquots added to the microtiter wells. The amount of antibody bound was determined using a goat anti-rabbit antibody conjugated to horseradish peroxidase. Absorbance readings were taken on the stopped reaction after 15 minutes. The enzyme substrate used was o-phenylene diamine. The results are shown in FIG. 2, in which A is readings before, and B is readings after, treatment with BSA beads.

Two other fluazifob conjugates were prepared to test these preparations further.

1) Fluazifob was linked to BSA using a β-alanine linker. The titer for fluazifob in the ELISA assay was measured against conjugate both with and without the β-alanine linker.

Figure 1:
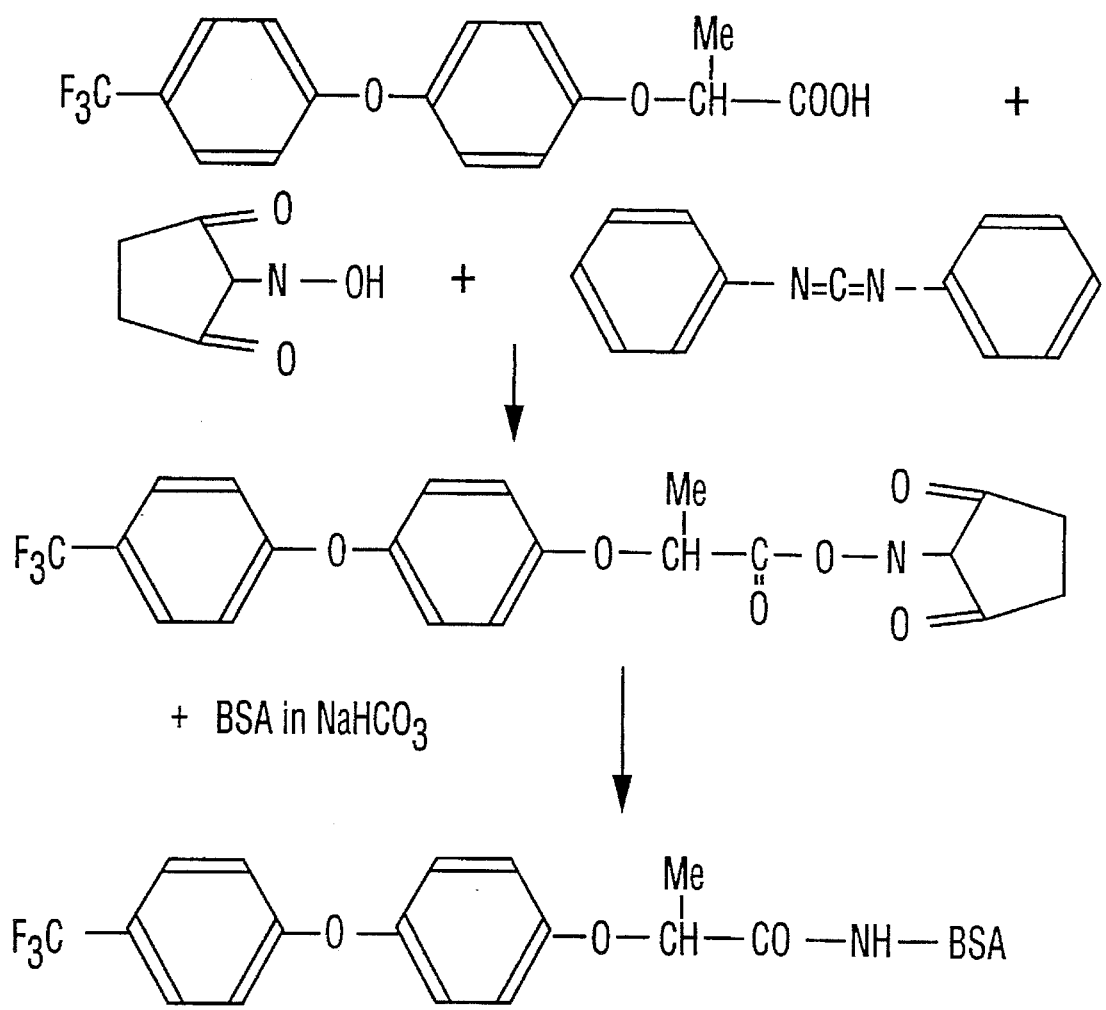
FIG. 1 represents schematically fluazifob-BSA conjugate preparation.

2) A conjugate between DL-2-phenoxypropionic acid and BSA was prepared and tested, since the phenoxypropionic acid structure, as can be seen in FIG. 1, is present in fluazifob. This structure might react as the major epitope in the fluazifob preparations, and might also be the site of linker directed anti-bodies. The conjugate was coupled to BSA beads using glutaraldehyde, and used to treat the serum that had been stripped of the anti-BSA antibodies.

The conjugate, DL-2-phenoxypropionic acid-BSA, was also used to test the response of the purified globulins solution to DL-2-phenoxypropionic acid.

The following procedure was used for these tests. Microtiter plate wells were coated with fluazifob-BSA and the reacted protein was added to each well so that the maximum reading of fully reacted material fell in the absorbance range of 1.0–1.5. To assay fluazifob concentrations, preparations of the antibody were mixed with fluazifob containing solutions, reacted for 5 minutes, added to the fluazifob-BSA coated well, and incubated for 30 minutes. After washing, all wells were reacted with the second antibody, and the absorbance of the well contents determined as described earlier. All readings were taken in triplicate.

Figure 3:
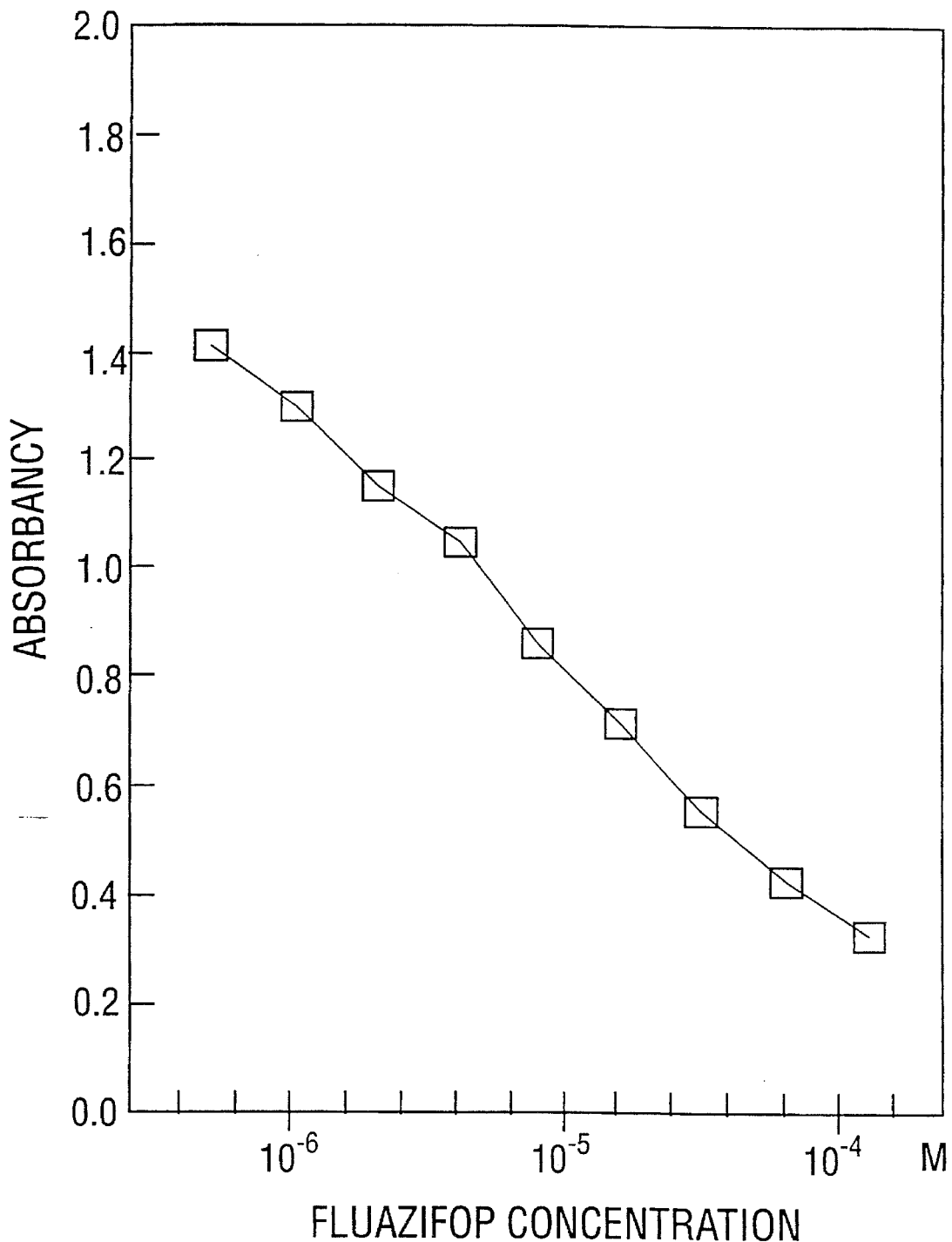
FIG. 3 represents fluazifob determinations in solutions.
Figure 4:
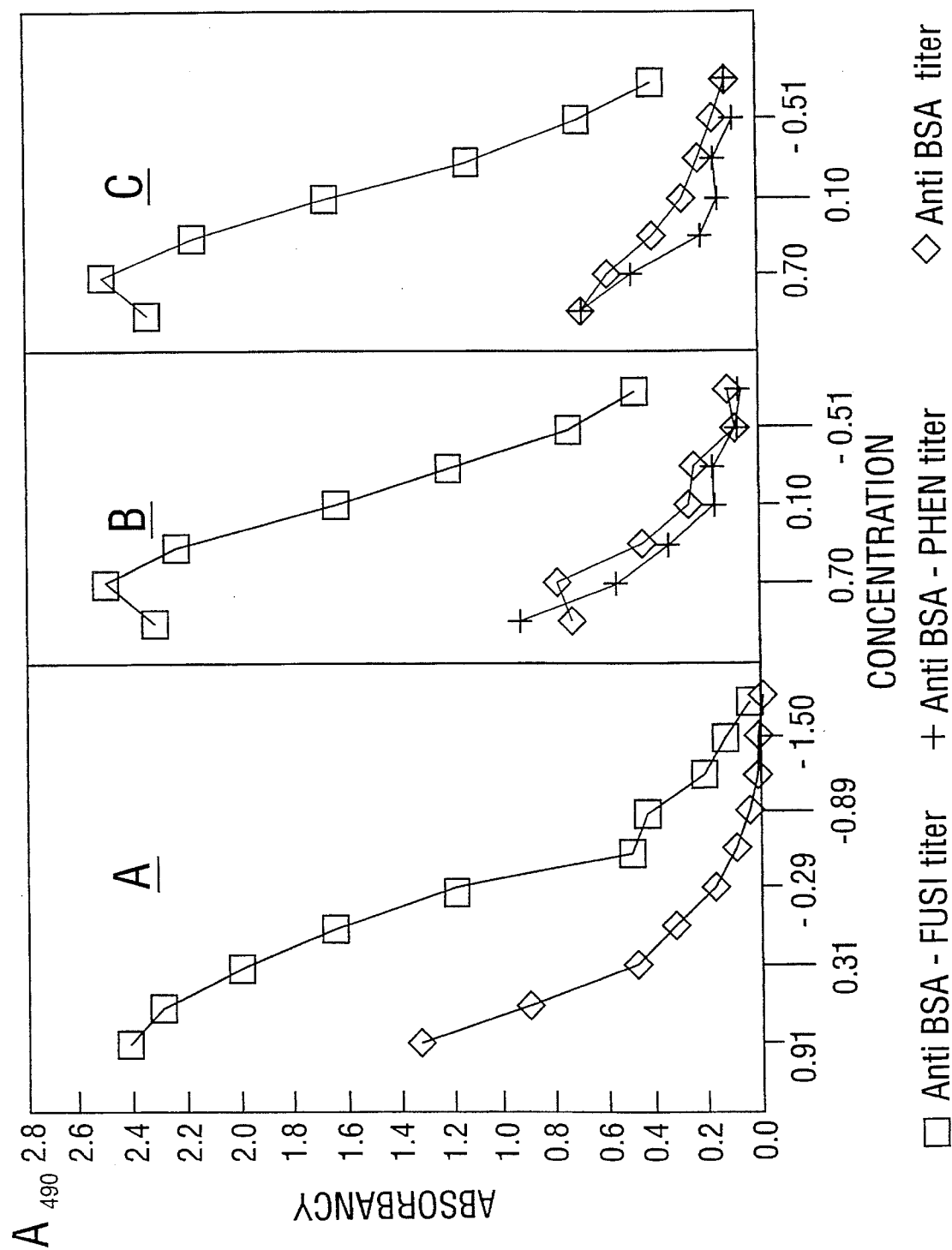
FIG. 4 represents anti-fluazifob and anti-phenoxy-propionic acid serum titers.
Figure 5:
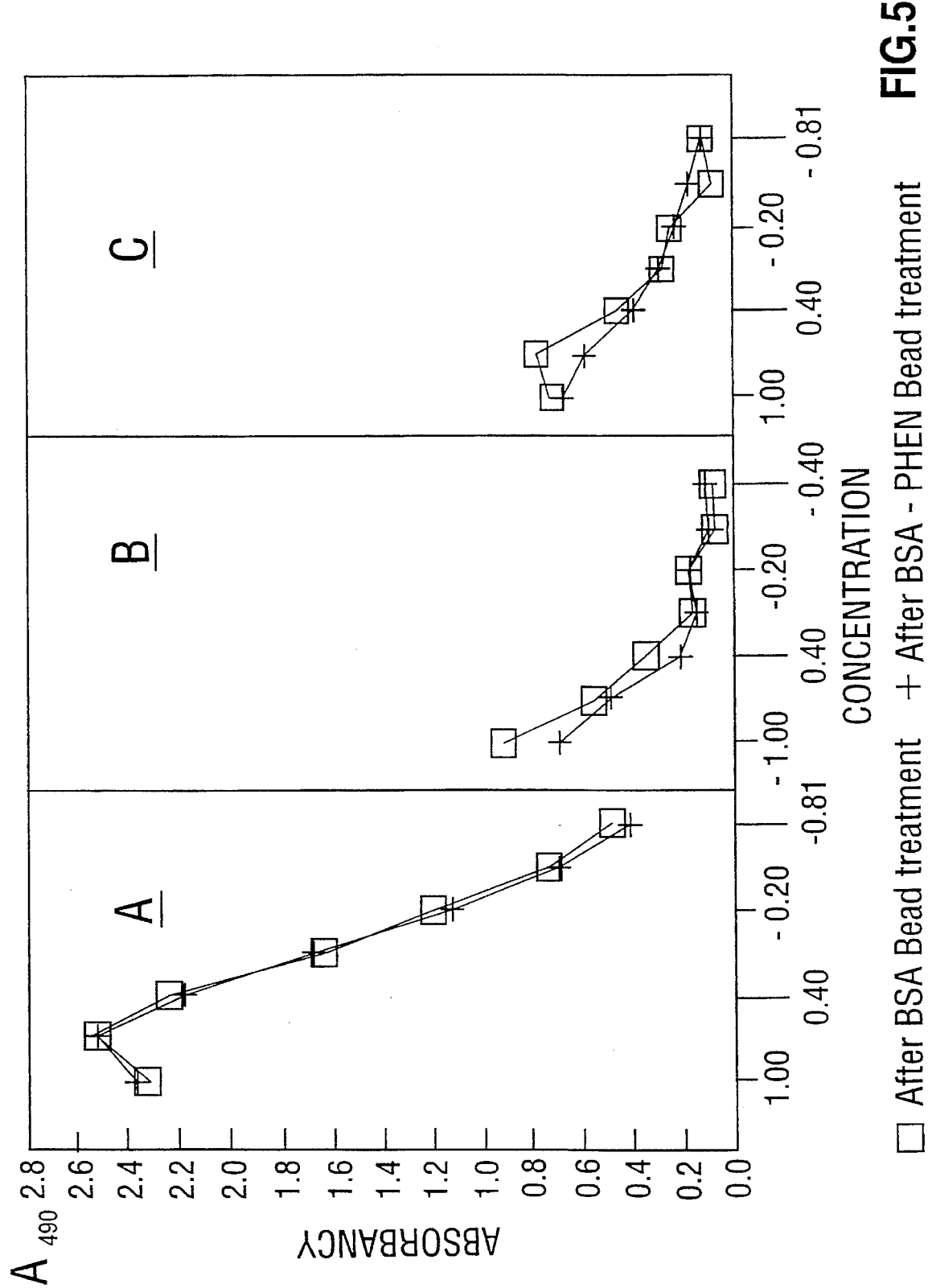
FIG. 5 represents antibody preparation titers against fluazifob, phenoxypropionic acid, and BSA.

The results, which are in FIGS. 3, 4 and 5, show that there was no response to the DL-2-phenoxypropionic acid (FIG. 3). This indicates, as is shown in FIGS. 4 and 5, that the activity of the antibody is directed to the pyridyl ring structure in fluazifob, and not to the carrier-linker area. In FIG. 4, part A shows the original IgG preparation, part B is after BSA bead treatment, and part C is after BSA-phenoxy bead treatment. In FIG. 5 the preparations were re-titered to determine if treatment with DL-2-phenoxypropionic acid-BAS beads changed the response of the antibody preparation. Part A shows the anti BSA-fluzaifob response, part B shows the BSA-phenoxy response, and part C the anti BSA response.

It is also apparent that using the microporous beads in both assays speeded up the preparation, since they could be used easily in a batch system. In addition, the beads are technically extremely easy to use, and give high activity preparations which can, in most instances, be used directly in ELISA procedures.

EXAMPLE 2

Preparation of BSA Polymer Beads

To 2 g BSA (Sigma A-4503; trademark) dissolved in 6 ml of an 0.5 M sodium carbonate/sodium bicarbonate buffer having a pH of 9.8 is added 30 ml of 2% lecithin solution comprising lecithin-0-phosphatidyl chloride solubilized in an organic solvent, which is a mixture of cyclohexane/chloroform, 80:20 v/v. The mixture is stirred mechanically at room temperature for about 1 minute. To this is then added 30 ml of a 5.0% mixture of terephthaloyl chloride in the cyclohexane/chloroform, 80:20 v/v mixture. At this level, the terephthaloyl chloride is not fully soluble, but can be adequately suspended by agitation. The mixture is then stirred using a mechanical stirrer at 5,000 rpm for about 35 minutes at room temperature. If necessary, further organic solvent mix is added. The beads are allowed to settle, and the organic solvents decanted from the beads. The beads are then washed in two steps. First, 5–10 ml of a solution of 10 parts by volume glycerol, and 1 part by volume TWEEN 20 trademark; a surfactant comprising a polyoxyethylene derivative of a fatty acid partial ester of sorbitol anhydride) are added and the beads stirred, followed by addition of about 50 ml of distilled water. The beads are separated from the first wash liquid by filtration (Buchner filter, coarse glass frit). Second, the beads are redispersed in about 100 ml of a glycerol-water mix, 80:20 v/v. The beads are refiltered, rinsed with a further 100 ml of the same glycerol-water mix, and refiltered. The beads are dried in a desiccator under vacuum and over calcium sulphate. They may also be stored in this dry state for extended periods of time.

EXAMPLE 3

Activation of the BSA Beads and Use

A suitable size column fitted with a 2-way stopcock and provided with an end cap is pre-rinsed in absolute ethanol and air dried in a nitrogen flow, to ensure that the internal surfaces and the filter is clean and dry. 100 mg of dried beads of BSA are introduced into the column, followed by 5 ml of degassed sodium phosphate buffer (0.02 M, pH 7.4). The column is placed under vacuum, and incubated for 20 minutes. During this time, the beads swell, and the hydrated beads are almost 5 times larger than the original dry beads. The swollen beads have a gel texture, a very smooth surface, and are somewhat translucent.

After the incubation period, the phosphate buffer is removed, and the beads rinsed with PBS solution (sodium phosphate, 0.02 molar, sodium chloride 0.15 molar, pH; 7.4). For use in processing serum of antibody preparations, 1 ml. of the serum of antibody solution is then added, and the column incubated at room temperature for up to 30 minutes with gentle agitation.

The serum is diluted if necessary with PBS solution to a maximum concentration of 2 mg protein per ml. The serum is drained from the column, the column washed with 1 ml. PBS solution, and two liquids combined together. The resulting solution is analyzed for protein concentration and activity.

EXAMPLE 4

Coating of BSA Beads with BSA with BSA or Alternate Carriers

An additional treatment of the beaded material from example 2 with the BSA can be used to prepare a material active with BSA or other carriers.

After soaking the BSA beads in phosphate buffer, as described in Example 2, the buffer was removed, and a solution of 2–5% glutaraldehyde solution in water was introduced. The column is then placed in a desiccator with a gas exhaust, and the air replaced with nitrogen, by placing the desiccator under vacuum and flushing with nitrogen. The vacuum/flush cycle was repeated five times. The beads were held under nitrogen for 90 minutes. The glutaraldehyde solution was then removed, and 5 ml of a BSA solution containing 10 mg BSA per ml of PBS was introduced. The column is then incubated for 2 hours at room temperature, with intermittent shaking. At the end of this period, the remaining liquid is removed; the column is then ready for use.

Suitable solutions of proteins other than BSA can be used in this procedure, such as ovalbumin, KLH, or Protein A, and multiple antigen peptide constructs containing T and B cell epitopes to provide BSA beads with an activated protein coating.

EXAMPLE 5

Microporous Beads—Binding Capacity Testing

Antibody preparations for testing were diluted to approximately 0.01 g/ml, and 100 l(microtiter) aliquots were added to microtiter wells. Two sets of wells had been precoated with either with BSA, or with fluazifob-BSA conjugate. After incubation for 30 minutes, each set of wells was washed to remove remaining unbound antibodies, and the presence of bound antibody assayed with goat anti-rabbit peroxidase, using ortho-phenylene diamine as substrate, and a sulphuric acid stop solution. Readings were taken at 490 nm, after a 15 minute reaction period and used to calculate the ratio of $A_{490nm}$ fluazifob/BSA wells to $A_{490nm}$ BSA wells. All readings were made in triplicate.

Three antibody containing solutions were tested:
Sample A: Rabbit serum after ammonium sulphate treatment and batch treatment with DEAE treated serum.
Sample B: Sample A was treated by chromatography on a column of BSA linked to the commercial material AFFI-GEL trademark; N-hydroxy-succinimide treated agarose from BoiRad). The best fraction from the column chromatography was taken for testing.
Sample C: Sample A after batch treatment with microporous BSA beads as described in Example 3. The treatment period was 2 hours.

The ELISA microtiter plate readings are summarized in the following Table:

TABLE 1

| Sample | Adsorption Readings at 490 nm | | Ratio* |
|---|---|---|---|
| | BSA Well | Fluazifob/BSA Well | |
| A | 0.371 | 0.844 | 2.27 |
| B | 0.147 | 0.905 | 6.16 |
| C | 0.094 | 1.022 | 10.87 |

*The ratio is fluazifob BSA well/BSA well.

It will be noted from the ratio values obtained with Sample A that anti-fluazifob antibodies were present in the antibody preparation. The ratio suggests that the anti-fluazifob antibodies were present in twice the concentration of the anti-BSA antibodies. This sample could however not be used in an ELISA procedure for assaying fluazifob since the background anti-BSA readings were so high.

Affinity purification of the Sample A antibody preparation by treatment with a column of BSA linked to AFFIGEL resulted in a preparation which was useable in the ELISA procedure. The entire process took more than 3 days, however, before the results were known.

Batch treatment of Sample A with microporous BSA beads as described in Example 3 resulted in a preparation (Sample C) of anti-fluazifob antibodies. The microporous beads were prepared as given in Example 2. The final preparation could be used directly in the ELISA procedure. Measurements of fluazifob into the micromolar range were readily done using the preparation. The overall time taken to achieve the result was less than 4 hours.

Thus, it can be seen that simple exposure to the cross-linked BSA carrier beads (Sample C), on the one hand, removes the BSA carrier antibodies effectively, without any apparent effect on the antibodies for fluazifob. This treatment step is simple and straight-forward. The residual serum from this step can then be used directly in an anti-hapten assay.

Further, although the procedure for (Sample C) used a 2 hour contact period, nevertheless, the antibody removal in the wells took place in 15 minutes. It is therefore apparent that this procedure is both simple, fast, and efficient.

The embodiments of the invention in which an exclusive property or privilege is claimed are defined as follows:

1. A method for removing anticarrier antibodies from a mixture of antibodies contained in a liquid medium, which mixture was generated in a host animal in the presence of the antigenic carrier, which process comprises:

(i) contacting the liquid medium containing the mixture of antibodies with a high surface area solid form of the same antigenic carrier;

(ii) incubating the solid form of the antigenic carrier in contact with the medium containing the mixture of antibodies at a temperature, and for a time period, sufficient for adsorption of the anticarrier antibodies by the solid form of the antigenic carrier to be substantially complete; and (iii) thereafter separating the solid form of the antigenic carrier together with the adsorbed anticarrier antibodies from the liquid medium.

2. A method according to claim 1, wherein the high surface area solid form of the antigenic carrier is the antigenic carrier in cross-linked form coated onto a surface.

3. A method according to claim 1, wherein the high surface area solid form of the antigenic carrier is the antigenic carrier in the form of beads.

4. A method according to claim 3, wherein the beads are the antigenic carrier in a cross-linked or polymerized form.

5. A method according to claim 1, wherein the antigenic carrier is a protein, and the solid form of the antigenic carrier is the protein in a polymerized or cross-linked form.

6. A method according to claim 5, wherein the protein is bovine serum albumin.

7. A method according to claim 3, wherein the beads are the antigenic carrier in cross linked form coated onto an inactive core.

* * * * *